United States Patent [19]

Weitz et al.

[11] Patent Number: 4,468,525
[45] Date of Patent: Aug. 28, 1984

[54] PREPARATION OF DIACYLOXYHEXADIENES FROM HEXATRIENES

[75] Inventors: Hans-Martin Weitz, Bad Durkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 490,152

[22] Filed: Apr. 29, 1983

Related U.S. Application Data

[62] Division of Ser. No. 287,278, Jul. 27, 1983, abandoned.

[30] Foreign Application Priority Data

Aug. 16, 1980 [DE] Fed. Rep. of Germany ....... 3030997

[51] Int. Cl.$^3$ ............................................. C07C 67/055
[52] U.S. Cl. ...................................... 560/244; 360/262
[58] Field of Search ......................................... 560/244

[56] References Cited

U.S. PATENT DOCUMENTS

| | | | |
|---|---|---|---|
| 3,755,423 | 8/1973 | Onoda | 560/244 |
| 3,872,163 | 3/1975 | Shimizu | 560/244 |
| 3,922,300 | 11/1975 | Onoda | 560/244 |
| 4,121,039 | 10/1978 | Parthasarthy | 560/244 |
| 4,131,743 | 12/1978 | Yoshida | 560/244 |
| 4,225,727 | 9/1980 | Kamiyama | 560/244 |
| 4,233,455 | 11/1980 | Weitz | 560/244 |

Primary Examiner—Michael L. Shippen
Attorney, Agent, or Firm—John H. Shurtleff

[57] ABSTRACT

A process for the preparation of a diacyloxyhexadiene of the formula

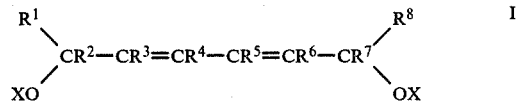

where X is $R^9$-CO- and $R^1$ to $R^9$ are hydrogen or alkyl of 1 to 3 carbon atoms, by reacting a hexatriene of the formula

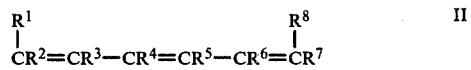

with oxygen and a carboxylic acid of the formula $R^9$COOH in the presence of a catalyst which contains palladium, platinum or a salt of these metals.

9 Claims, No Drawings

PREPARATION OF DIACYLOXYHEXADIENES FROM HEXATRIENES

This application is a division of application Ser. No. 287,278, filed July 27, 1983 now abandoned.

The present invention relates to a process for the preparation of diacyloxyhexadienes by reacting hexatrienes with oxygen and carboxylic acids in the presence of catalysts.

It is known that 1,3-butadiene, which can be alkyl-substituted or acyloxy-substituted, can be reacted with oxygen and carboxylic acids in the presence of palladium-containing or platinum-containing catalysts to give but-2-ene-1,4-diol diesters and but-1-ene-3,4-diol diesters. Homogeneously dissolved catalysts, or supported catalysts, can be used for this purpose.

Thus, for example, according to British Pat. No. 1,138,366 reaction of piperylene with air in the presence of palladium acetate, copper acetate and lithium acetate dissolved in glacial acetic acid gives a mixture of 1,4-diacetoxy-pent-2-ene and 4,5-diacetoxy-pent-2-ene in the molar ratio of 4:1. Similarly, reaction of 1,3-butadiene with oxygen in the presence of palladium acetate, copper acetate and potassium acetate dissolved in glacial acetic acid gives, according to British Pat. No. 1,277,837, 1,4-diacetoxy-but-2-ene.

German Pat. No. 2,217,452 describes a process for the acetoxylation of butadiene, wherein a supported palladium catalyst which additionally contains antimony, bismuth, tellurium or selenium is used. The acetoxylation described in German Laid-Open Application DOS No. 2,728,574 is carried out in the presence of a sulfur-containing supported palladium catalyst which can additionally contain other elements. According to German Laid-Open Application DOS No. 2,820,519, a supported catalyst which contains palladium and copper in the form of an intermetallic compound is used. German Laid-Open Application DOS No. 2,417,558 describes supported platinum catalysts which additionally contain one of the elements phosphorus, arsenic, antimony, selenium or tellurium. The reaction of butadiene with oxygen and acetic acid, ie. acetoxylation, in the presence of the said catalysts results very predominantly in cis- and trans-but-2-ene-1,4-diol diacetates, with but-1-ene-3,4-diol monoacetate and diacetate being formed in only very minor amounts.

We have found, surprisingly, that reaction of 1,3,5-hexatrienes with oxygen and carboxylic acids in the presence of palladium, platinum or salts of these metals gives 1,6-diacyloxy-2,4-hexadienes.

According to the process of the invention, a diacyloxyhexadiene of the formula

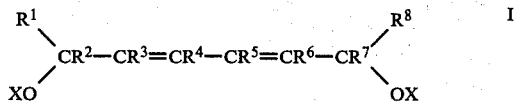

where X is $R^9$—CO— and $R^1$ to $R^9$ are hydrogen or alkyl of 1 to 3 carbon atoms is obtained by reacting a hexatriene of the formula

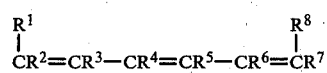

with oxygen and a carboxylic acid of the formula $R^9COOH$ in the presence of a catalyst which contains palladium, platinum or a salt of these metals.

For the case of the reaction of 2,4,6-octatriene (1,6-dimethyl-1,3,5-hexatriene) with acetic acid and oxygen, to give 2,7-diacetoxy-3,5-octadiene (1,6-dimethyl-1,6-diacetoxy-2,4-hexadiene), the reaction can be represented by the following equation (where —OAc— = —O—CO—CH$_3$):

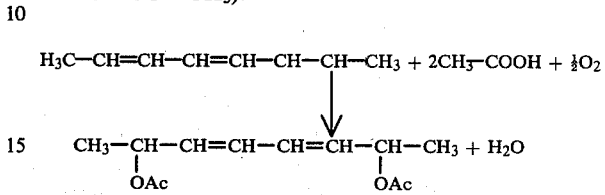

It was not foreseeable whether 1,3,5-hexatrienes would react at all with oxygen and carboxylic acids to give defined products and whether, if the reaction did occur, the products would be predominantly 1,6-diacyloxy-2,4-hexadienes, 1,4-diacyloxy-2,5-hexadienes or 3,4-diacyloxy-1,5-hexadienes. It might also have been expected that the air-sensitive 1,3,5-hexatrienes might polymerize extensively under the reaction conditions, in the presence of oxygen.

According to the process of the invention, the diacylate of the formula I is obtained from the hexatriene of the formula II by a one-stage acyloxylation. Hitherto, a multi-stage reaction has been required to prepare 1,6-diacetoxy-2,4-hexadiene. Thus, 1,5-hexadiene (diallyl) has been brominated with N-bromosuccinimide, 3,4-dihydroxy-1,5-hexadiene with phosphorus tribromide or 1,3,5-hexatriene with bromine, to give 1,6-dibromo-2,4-hexadiene, which on reaction with silver acetate or sodium acetate is converted to 1,6-diacetoxy-2,4-hexadiene. (P. Karrer, W. Ringli, Helv. Chim. Acta 30 (1947), 1771; Ch. Prévost, Comp. Rend. 184 (1927), 458).

The diacyloxyhexadienes of the formula

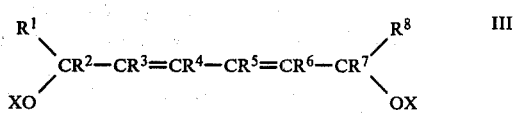

obtainable according to the invention, where X is $R^9$—CO— and $R^1$ to $R^9$ are hydrogen or alkyl of 1 to 3 carbon atoms are novel compounds, with the exception of 1,6-diacetoxy-2,4-hexadiene.

The novel diacyloxyhexadienes of the formula

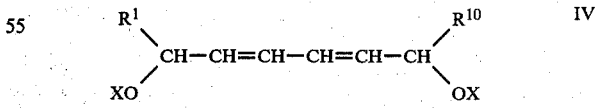

where X is $R^9CO$—, $R^1$ and $R^9$ are hydrogen or alkyl of 1 to 3 carbon atoms and $R^{10}$ is alkyl of 1 to 3 carbon atoms, and especially the compounds of the formula

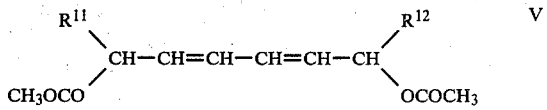

where $R^{11}$ is hydrogen, methyl or ethyl and $R^{12}$ is methyl or ethyl, are of particular industrial interest.

Examples of starting materials of the formula II are 1,3,5-hexatriene, 1,3,5-heptatriene, 1,3,5-octatriene and 2,4,6-octatriene. The triolefins can be employed as individual compounds or as mixtures which can, for example, also contain other hydrocarbons, such as monoolefins and paraffin hydrocarbons.

The starting compounds mentioned can be prepared, for example, by eliminating water from the corresponding dienols. Thus, 1,3,5-hexatriene can be obtained by dehydrating 1,3-hexadien-1,5-ol, and 1,3,5-octatriene by dehydrating 2,4-octadien-6-ol (K. Alder and H. v. Brachel, Liebigs Ann. Chem. 608 (1957) 195). 2,4,6-Octatriene can be prepared, for example, by dimerizing butadiene to give 1,3,7-octatriene (German Laid-Open Application DOS No. 1,443,442) and then isomerizing this compound by means of a palladium compound (Japanese patent application No. 50,601 (1972)).

Suitable carboxylic acids are formic acid, acetic acid and propionic acid.

The catalysts used are palladium, platinum or salts of these metals, and can additionally contain other active constituents. For example, supported catalysts which contain, as active constituents, palladium or platinum plus copper and/or tellurium, applied to a carrier, can be used.

The catalysts suitable for the process according to the invention can be prepared in a conventional manner, for example as described in German Pat. No. 2,217,452 or German Laid-Open Application DOS No. 2,820,519 or DOS No. 2,417,558. Catalysts of the type mentioned for example contain from 1 to 10% of palladium or platinum, from 0.1 to 30% of copper and/or from 0.01 to 10% of tellurium, in each case based on catalyst weight. Preferably, a supported catalyst which contains from 0.01 to 6, preferably from 1 to 3.5, gram atoms of copper and/or from 0.01 to 1, preferably from 0.01 to 0.4, gram atom of tellurium per gram atom of palladium or platinum is used.

The total amount of catalytically active metals applied to the carrier is advantageously, for example, from 0.01 to 30% by weight, based on supported catalyst. However, higher and lower concentrations can also be used.

Examples of suitable carrier materials for the catalysts are active charcoal, bauxite, pumice, silica gel, kieselguhr and other forms of silica, magnesia, clay and alumina.

The catalytically active metals can also be used without a carrier, by dissolving or suspending a salt of the metal in the reaction mixture.

The preparation of the diacyloxyhexadienes is carried out in a conventional manner, in the gas phase or liquid phase, at from 70° to 180° C. The gas phase reaction is preferably carried out at from 120° to 150° C. and the liquid phase reaction preferably at from 70° to 110° C. The reaction pressure depends on the process used and can be from atmospheric pressure to, for example, 100 bar. The process can be carried out batchwise or continuously, for example in a fixed bed, fluidized bed or three-phase fluidized bed.

The diacyloxyhexadienes obtainable by the process of the invention are valuable intermediates. On hydrogenation and hydrolysis they give substituted hexanediols which, as in the case of hexane-1,6-diol (Ullmanns Encyklopädie, Volume 7, page 228) and of 1,8-octanediol (German Laid-Open Application DOS No. 1,066,566), can be used, for example, to prepare polyurethanes, esters and plasticizers.

In the Examples, percentages are by weight.

EXAMPLE 1

(a) Preparation of the catalyst 89.6 g of copper powder are dissolved in 660 cm$^3$ of 33% strength nitric acid and this solution is mixed, at room temperature, with a solution of 83.4 g of PdCl$_2$ in 400 cm$^3$ of a warm 1:1 (by volume) mixture of 66% strength nitric acid and 32% strength hydrochloric acid, and with a solution of 6.25 g of TeO$_2$ in 1,000 cm$^3$ of warm 16% strength hydrochloric acid. 1,000 g of active charcoal (0.3–0.5 mm) are stirred for 5 hours at 70° C. with 15% strength nitric acid, filtered off, washed neutral and dried under reduced pressure at 150° C. The combined metal salt solution is added to this active charcoal, and thereafter sufficient water is added to ensure that the charcoal is wetted completely.

The material is then evaporated to dryness on a rotary evaporator at 85° C. under a water pump vacuum. The catalyst obtained is dried for 2 hours at 150° C. in a reduced pressure drying oven and then for 2 hours at 150° C. in a tubular furnace under a stream of nitrogen. Thereafter, activation is effected by passing nitrogen, saturated with methanol at room temperature, over the catalyst at 400° C. and finally passing hydrogen (at the rate of 20 liters per hour) over the catalyst at 800° C. for half an hour. The catalyst is then allowed to cool to room temperature under a stream of nitrogen.

According to elementary analysis, the catalyst contains 5.04% of palladium, 8.2% of copper and 0.55% of tellurium.

(b) Acetoxylation of octatriene

An apparatus consisting of a 1 liter three-necked flask equipped with an Anschütz attachment, dropping funnel, gassing stirrer, internal thermometer, gas inlet tube and reflux condenser surmounted by a solid carbon dioxide condenser is flushed with nitrogen. A suspension of 25 g of the catalyst prepared in Example 1(a), in 543 g of glacial acetic acid, is then introduced into the apparatus. The mixture is heated to 95° C. and 12 liters of oxygen are introduced in the course of 4 hours, whilst at the same time adding 54 g of 2,4,6-octatriene dropwise. A further 1.5 liters of oxygen are then introduced in the course of 30 minutes at 95° C., after which the apparatus is flushed with nitrogen for 30 minutes. The mixture is allowed to cool and the catalyst is filtered off. The acetic acid solution obtained (603 g) is evaporated down on a rotary evaporator. Fractional distillation of the residue (92 g) gives 61.3 g of a mixture of isomeric diacetoxyoctadienes (54% yield based on 2,4,6-octatriene employed), of boiling point 104°–113° C./1 mbar. According to analysis by gas chromatography, this mixture contains 52% of 2,7-diacetoxy-3,5-octadiene (1,6-dimethyl-1,6-diacetoxy-2,4-hexadiene) which crystallizes out from the mixture on cooling; melting point 74°–75° C. (after recrystallization from xylene).

EXAMPLE 2

Following a similar procedure to Example 1(b), 6 liters of oxygen are introduced, and 26 g of 1,3,5-octatriene are dripped, in the course of 2 hours at 95° C., into a suspension of 12.5 g of a catalyst, prepared according to German Laid-Open Application DOS No. 2,820,519 and containing 5.27% of Pd and 8.59% of Cu on an active charcoal carrier, in 543 g of acetic acid. A further 1.5 liters of oxygen are then introduced in the course of 30 minutes at 95° C., after which the apparatus is flushed with nitrogen for 30 minutes. After working up as described in Example 1(b), and subjecting the acetic acid solution (564 g) to fractional distillation, 23.9 g of a mixture of isomeric diacetoxyoctadienes (42% yield, based on 1,3,5-octatriene employed), of boiling point 90°–110°/0.5 mbar, are obtained, the main product in the mixture being 1,6-diacetoxy-2,4-octadiene (1,6-diacetoxy-6-ethyl-2,4-hexadiene).

EXAMPLE 3

Following a similar procedure to Example 1(b), 6 liters of oxygen are introduced, and 18.6 g of 1,3,5-hexatriene are dripped, in the course of 2 hours at 95° C., into a suspension of 12.5 g of a catalyst, prepared according to German Laid-Open Application DOS No. 2,217,452 and containing 5.27% of Pd and 0.51% of Te on an active charcoal carrier, in 540 g of acetic acid. A further 1.5 liters of oxygen are then introduced in the course of 30 minutes at 95° C., after which the apparatus is flushed with nitrogen for 30 minutes. After working up and distillation, 20.5 g of a mixture of isomeric diacetoxyhexadienes (44% yield, based on 1,3,5-hexatriene employed) of boiling point 73°–98° C./0.5 mbar are obtained. According to analysis by gas chromatography, this mixture contains 60% of 1,6-diacetoxy-2,4-hexadiene, which crystallizes out on cooling; melting point 22°–25° C. (after recrystallization from diisopropyl ether).

We claim:

1. A process for the preparation of a diacyloxyhexadiene of the formula

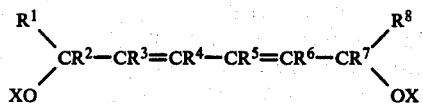

where X is $R^9$—CO— and $R^1$ to $R^9$ are hydrogen or alkyl of 1 to 3 carbon atoms, which comprises reacting a hexatriene of the formula

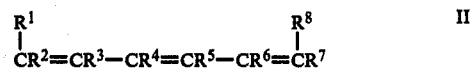

with oxygen and a carboxylic acid of the formula $R^9COOH$ in the presence of a catalyst which contains palladium or platinum or a salt of these metals.

2. A process as claimed in claim 1, wherein the reaction is carried out in the gas phase or liquid phase at from 70° to 180° C.

3. A process as claimed in claim 2 wherein the reaction is carried out in the gas phase at from 120° to 150° C.

4. A process as claimed in claim 2 wherein the reaction is carried out in the liquid phase at from 70° to 110° C.

5. A process as claimed in claim 1 wherein the reaction is carried out at atmospheric pressure up to about 100 bar.

6. A process as claimed in claim 1 wherein the diacyloxyhexadiene of the formula I is obtained from the hexatriene of the formula II in a one-stage acyloxylation.

7. A process as claimed in claim 2 wherein the diacyloxyhexadiene of the formula I is obtained from the hexatriene of the formula II in a one-stage acyloxylation.

8. A process as claimed in claim 1 wherein the catalyst is carrier supported and contains, in addition to said palladium, platinum or salts thereof, at least one other active constituent selected from the group consisting of copper and tellurium.

9. A process as claimed in claim 8 wherein the catalyst contains, based on the catalyst weight, 1 to 10% of palladium and/or platinum with the addition of 0.1 to 30% of copper and/or 0.1 to 10% of tellurium.

* * * * *